United States Patent [19]

Rangert et al.

[11] Patent Number: 5,069,622
[45] Date of Patent: * Dec. 3, 1991

[54] SPACER

[75] Inventors: Bo Rangert, Mölnlycke; Lars Jörnéus; Claes Holmberg, both of Gothenburg; Matts Andersson, Fåker, all of Sweden

[73] Assignee: Nobelpharma AB, Gothenburg, Sweden

[*] Notice: The portion of the term of this patent subsequent to Mar. 19, 2008 has been disclaimed.

[21] Appl. No.: 512,499

[22] Filed: Apr. 20, 1990

Related U.S. Application Data

[63] Continuation of Ser. No. 271,824, Nov. 16, 1988, abandoned.

[30] Foreign Application Priority Data

Nov. 18, 1987 [SE] Sweden .............................. 8704514

[51] Int. Cl.$^5$ ............................................. A61C 8/00
[52] U.S. Cl. ..................................................... 433/173
[58] Field of Search .................. 133/173, 174, 175, 176

[56] References Cited

U.S. PATENT DOCUMENTS

| | | | |
|---|---|---|---|
| 4,645,453 | 2/1987 | Niznick | 433/173 |
| 4,713,004 | 12/1987 | Linkow et al. | 433/174 |
| 4,780,080 | 10/1988 | Haris | 433/173 |
| 4,842,518 | 6/1989 | Linkow et al. | 433/174 |
| 4,854,872 | 8/1989 | Detsch | 433/174 |
| 4,907,969 | 3/1990 | Ward | 433/173 |

FOREIGN PATENT DOCUMENTS

| | | |
|---|---|---|
| 0216031 | 6/1986 | European Pat. Off. |
| 0313222 | 4/1989 | European Pat. Off. |
| WO8300616 | 3/1983 | PCT Int'l Appl. |
| 8803007 | 5/1988 | PCT Int'l Appl. |
| 2176709 | 1/1987 | United Kingdom .............. 433/174 |

Primary Examiner—Cary E. O'Connor
Attorney, Agent, or Firm—Pollock, Vande Sande & Priddy

[57] ABSTRACT

An angulated spacer element adapted is at its one end for attachment to a fixture having a threaded aperture and implanted in the jaw bone, and to support a dental prosthesis at the other end. The spacer element, which is a unitary member, has a first portion with an end surface thereof permitting abutting engagement with the protruding end of the implanted fixture. The first portion also has a through bore aligned with the threaded aperture in the fixture and defining an internal ledge to enable a screw to pass through the bore, abut the ledge and threadably engage the threaded aperture in the fixture. The first portion is adapted for locking the spacer element in a selectable one of a plurality of rotational, fixed positions in relation to the protruding portion of the fixture. The unitary spacer element also includes a second portion for supporting the dental prosthesis on the spacer element, the second portion forming an acute angle with respect to the through bore of the first portion.

10 Claims, 2 Drawing Sheets

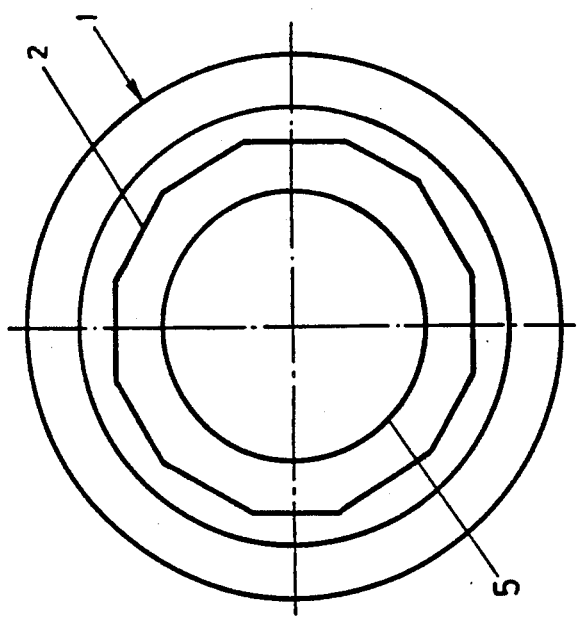
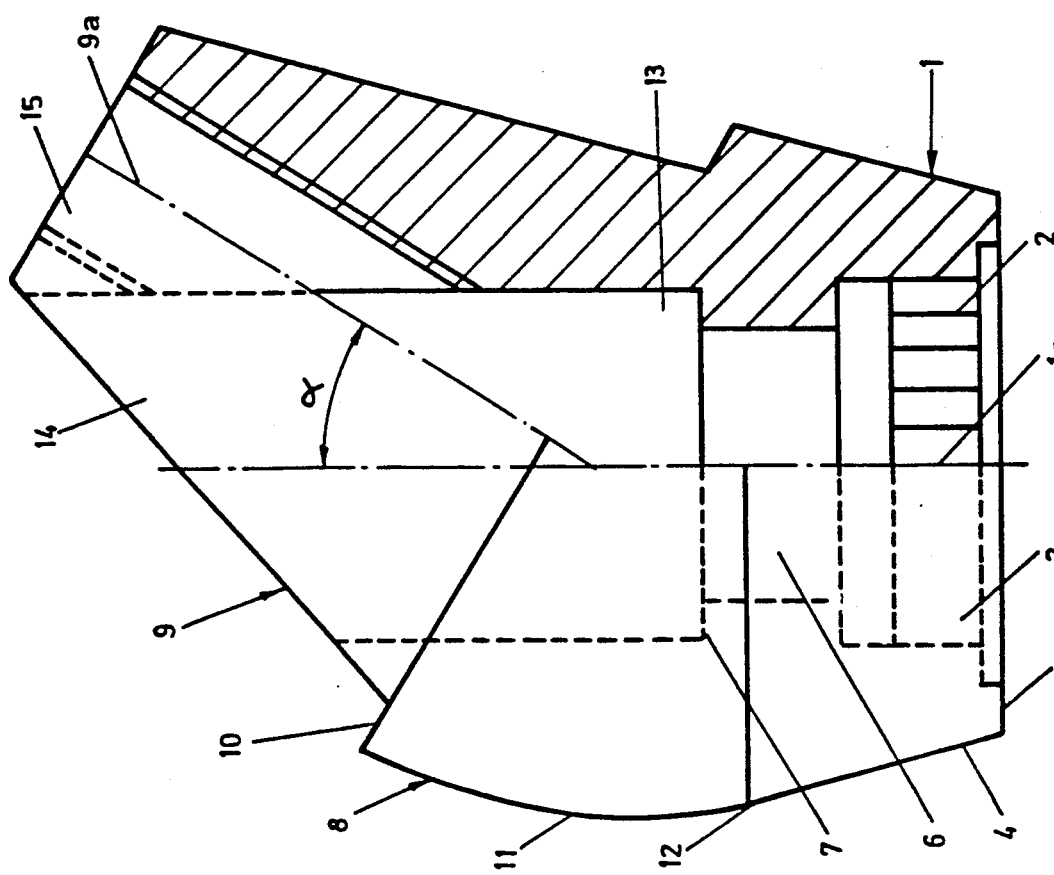

SPACER

This application is a continuation of Ser. No. 07/271,824, filed on Nov. 16, 1988 now abandoned.

TECHNICAL FIELD

The present invention relates to a spacer for a dental implant disposed between a fixture implanted in the jaw bone and a dental bridge or artificial tooth.

BACKGROUND OF THE INVENTION

It is previously known in this art to permanently anchor oral prostheses in the jaw bone by means of helical anchorage elements, so-called fixtures, of a biocompatible material, preferably pure titanium. That method which has proved to give the highest anchorage stability and which has been used clinically with considerable success for more than 20 years is the so-called osseo-integration method developed by Professor Per-Ingvar Brånemark et. al. and described in, for example, Brånemark/Zarb/Albrektsson: "Tissue-Integrated Prostheses", Quintessence Books, 1985.

The method is based on a highly exact and atraumatic implantation technique of the fixture such that direct contact, i.e. an exact adaptation without interjacent bonding tissue, takes place between the fixture and the bone tissue proper. Such a direct contact between fixture and bone tissue creates the best preconditions for a really permanent anchorage of a dental prosthesis.

The helical fixtures which are of pure titanium are surgically implanted in the jaw bone in a first operation which is followed by an unloaded healing phase of critical length during which time the fixture is covered by intact mucous membrane. During this healing phase, the bone tissue grows onto and forms a unit with the implanted fixture. In a second operation, the fixture is then exposed and a spacer is applied to the fixture with the aid of a spacer screw. The dental prosthesis, in the form of a bridge construction, is then anchored in place by means of an anchorage screw which in its turn anchors in the spacer screw.

A bridge construction is anchored with the aid of a plurality of fixtures, for example six in number, and corresponding spacers which constitute connection members between the bridge construction and the fixtures. In order to be able to accomodate the extreme oral loadings to which the screw connection is exposed, the spacer is made of a biocompatible material of extremely good mechanical strength properties, for example titanium or the like.

To impart increased flexibility to the implant system, it is previously known in this art to employ angled spacers, see for example U.S. Pat. No. 3,732,621, DE 35 31 389 and implant systems of the ROTUBMENT type. The reason for wishing, in certain cases, to angle the spacers is that, using conventional systems, the anchorage screw for the dental bridge may on occasions be located in an unsuitable position. By means of an angled spacer, the anchorage screw can be placed in a more favorable position from the points of view of cosmetic appearance and dental technology.

A factor common to all of the prior-art angled spacers is that they are adjustable, which is a considerable disadvantage since it is difficult to reestablish the exact position if the original setting is loosened. This makes it difficult to get a dental bridge in position if the original setting has been disrupted. Moreover, such constructions are mechanically flimsy and suffer from poor strength because they are based on a combination of a ball with a narrow neck.

A further disadvantage inherent in these prior-art constructions is that pockets occur where bacteria may gather and give rise to inflammation.

SUMMARY OF THE PRESENT INVENTION

The object of the present invention is to obviate the above-outlined drawbacks and problems and to provide an angled spacer in which both the connection direction and screw connection are angled in relation to the direction of the fixture. The solution to these problems is apparent from the characterizing clause of appended claim 1.

BRIEF DESCRIPTION OF THE ACCOMPANYING DRAWINGS

The nature of the present invention and its aspects will be more readily understood from the following brief description of the accompanying Drawings, and discussion relating thereto.

In the accompanying Drawings:

FIG. 1 is a side elevation, partly in section, of the angled spacer;

FIG. 2 is an end elevation of the spacer of FIG. 1;

DESCRIPTION OF ILLUSTRATIVE EMBODIMENT

Figure 4:
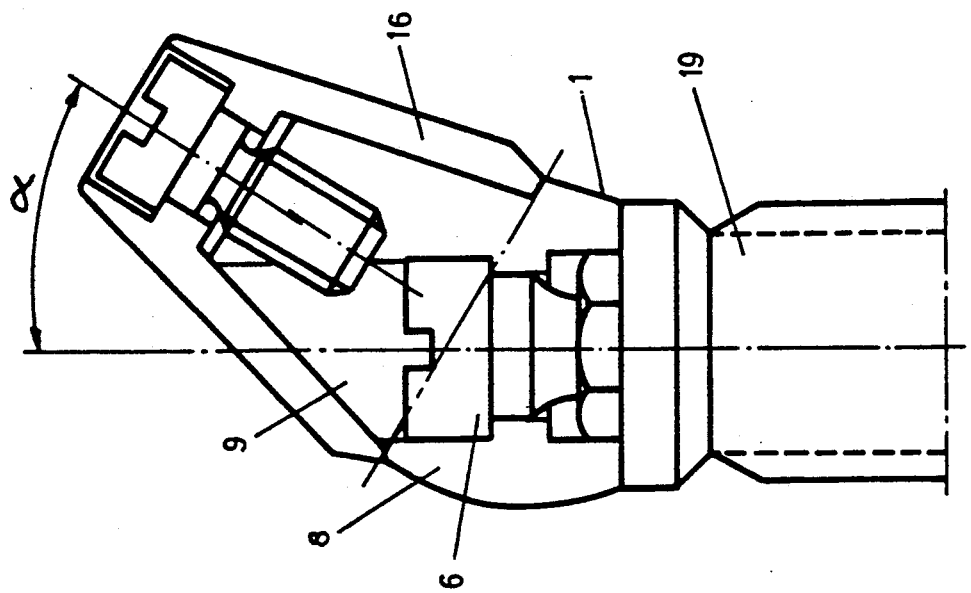
FIG. 4 is a schematic diagram showing the spacer assembled together with the fixture and connection sleeve.

Referring to the Drawings, the spacer includes a conical base portion 1 intended to cooperate with the upper portion of a fixture of that type which includes an upper hexagon. Such fixtures are previously known in the art and will not, therefore, be described in greater detail here. The base portion is disposed such that its line of symmetry 1a coincides with the line of symmetry of the fixture. The base portion is further designed so as to have interior dodecagonal geometrical configuration 2 which fits the hexagon of the fixture, implying that the spacer, on being turned, will have 30° instead of 60° between the directions of deviation, and an outer annular support surface 3 which abuts against the shoulder portion of the fixture. The conical circumferential surface 4 corresponds with good fit to the upper cylindrical side surface of the fixture so that the surface beneath the level of the gum will be completely smooth.

The dodecagonal "star" 2 constitutes a rotational lock and provides twelve fixed directions for the spacer.

The base portion further includes a cylindrical through-hole 5 for a spacer screw (not shown) intended to engage with the interiorly threaded bore in the upper portion of the fixture for fixedly locking the spacer to the fixture. The head 6 of the spacer screw (see FIG. 4) then abuts against an upper interiorly circular heel 7 in the spacer. The spacer screw may be a standard component included in the Nobelpharma Implant System.

At its top, the base portion 1 merges, via a segmented intermediate portion 8, into a conical upper portion 9 whose line of symmetry 9a is angled in relation to the line of symmetry 1a of the base portion. The angle of deviation α lies preferably within the range of between 25° and 40°, in this case at 32°. The base of the conical upper portion 9 merges in the segmented portion 8 via an annular shoulder 10 whose function will be described below.

The circumferential surface 11 of the segmented portion 8 connects at its bottom with an even transition 12 to the conical base portion, and the portion 8 is provided with an inner cylindrical cavity 13 for accommodating the screw head 6 of the above-mentioned spacer screw. Thus, the screw union which holds the spacer in place against the fixture is coaxial therewith and the spacer screw is passed in through a hole 14 in the conical circumferential surface of the upper portion. The conical upper portion 9 displays a relatively large conical angle, which facilitates connection of the dental bridge.

The conical upper portion 9 is provided with a threaded hole 15 for the screw union which unites the spacer with a sleeve cast in the dental bridge. Thus, the screw union is coaxial with this sleeve.

Figure 3:
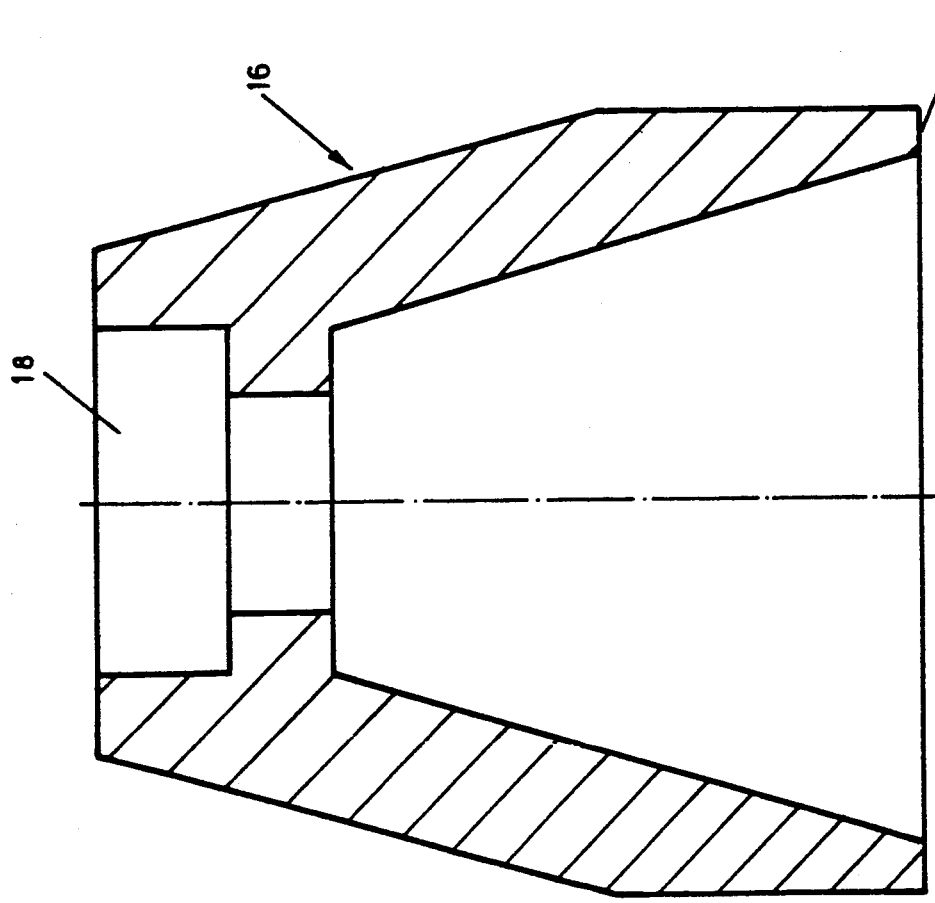
FIG. 3 shows a connection sleeve adapted to the angled spacer of FIG. 1.

A suitable connection sleeve 16 for the dental bridge is illustrated in FIG. 3. The sleeve is symmetrically circular and rests with its broader base 17 against the shoulder (abutment) 10 on the spacer. The sleeve is not in contact with the conical surface of the spacer. This is an advantage, since a conical connection always requires much greater precision and often entails that stresses are embodied in the construction. The upper portion of the sleeve includes a recess 18 for the screw union. The connection sleeve is cast, at a dental technology laboratory, in the dental bridge and is united therewith. It is also conceivable to make a direct casting of a dental bridge with holes whose inner surfaces are analogous with the connection sleeves.

It will be apparent from the above description that both the spacer and the dental bridge are secured by screw unions and with a fixed angle of deflection between both of the screw unions. The connection sleeve 16 covers the screw hole 14 in the upper region of that screw which unites the spacer with the fixture. Since the upper portion 9 of the spacer has been given a conical design, connection will be permitted of the dental bridge to several mutually diverging spacers.

The spacer is made of titanium or a titanium-containing material, while the connection sleeve may be made of gold.

Finally, FIG. 4 shows the spacer assembled together with a fixture 19 and a connection sleeve 16.

The present invention should not be considered as restricted to that described above and shown on the Drawings, many modifications being conceivable without departing from the spirit and scope of the appended claims.

What we claim and desire to secure by Letters Patent is:

1. An angulated spacer element adapted at its one end for attachment to a fixture having a threaded aperture and implanted in the jaw bone, said spacer element being adapted at its other end to support a dental prosthesis, comprising:

said spacer element being a unitary member;

said spacer element having a first portion with an end surface thereof permitting abutting engagement with the protruding end of the implanted fixture, said first portion also having a through bore aligned with said threaded aperture in the fixture and defining an internal ledge to enable a screw to pass through said bore, abut said ledge, and threadably engage the threaded aperture in the fixture;

said first portion having means for locking said spacer element in a selectable one of a plurality of rotational, fixed positions in relation to said protruding portion of said fixture;

said spacer element having a second portion for supporting the dental prosthesis on the spacer element, said second portion forming an acute angle with respect to said through bore of said first portion; and wherein said locking means is adapted to cooperate with an interlocking means provided on the protruding portion of the fixture and wherein one of said means is an n-sided polygon and the other means is a 2n-sided polygon.

2. An angulated spacer according to claim 1, wherein said first portion comprises a substantially conical base portion which cooperates with the protruding portion of the fixture, and said second portion comprises a substantially conical upper portion, and an intermediate portion is provided between said first and second portions.

3. An angulated spacer according to claim 2, wherein said fixed angle is within the range of between 25° and 40°.

4. An angulated spacer according to claim 2, further comprising a connection sleeve insertable between said second portion and said dental prosthesis which is adapted to cover said first through bore.

5. An angulated spacer according to claim 4, wherein said connection sleeve rests against a shoulder provided on said intermediate portion.

6. An angulated spacer for connecting a dental prosthesis to a fixture adapted for implantation in the jaw bone, said spacer comprising:

a single member having a lower portion and an angulated portion extending from said lower portion, said lower portion including locking means adapted to cooperate with the upper portion of the fixture for locking said member in a selected one of a plurality of fixed rotational positions relative to the fixture, said lower portion also including a first through bore having an axis aligned with the longitudinal axis of the fixture, said bore being adapted for receiving a first fastening means for fixing said member to the fixture in said selected rotational position, said angulated portion having an outer surface configured for receiving and supporting the dental prosthesis, said angulated portion including a second threaded through bore extending therein and having an axis forming a fixed angle with the axis of the first through bore, said second bore being adapted for receiving a second fastening means for securing the dental prosthesis to said angulated portion.

7. An angulated spacer according to claim 6, wherein said locking means has a dodecogonal configuration adapted to cooperate with a hexagonal head of the protruding portion of the fixture to provide twelve fixed rotational positions for the spacer.

8. An angulated spacer according to claim 6, wherein said fixed angle is within the range of between 25° and 40°.

9. An angulated spacer element adapted at its one end for attachment to a fixture having a threaded aperture and implanted in the jaw bone, said spacer element being adapted at its other end to support a dental prosthesis, comprising:

said spacer element being a unitary member;

said spacer element having a first portion with an end surface thereof permitting abutting engagement with the protruding end of the implanted fixture, said first portion also having a through bore aligned with said threaded aperture in the fixture and defining an internal ledge to enable a straight screw to pass through said bore, abut said ledge, and threadably engage the threaded aperture in the fixture;

said spacer element having a second portion for supporting the dental prosthesis on said spacer element, said second portion forming an acute angle with respect to said through bore of said first portion; and wherein said first portion comprises a substantially conical base portion which cooperates with the protruding portion of the fixture, and said second portion comprises a substantially conical upper portion.

10. An angulated spacer according to claim 9, further comprising a connection sleeve insertable between said second portion and the dental prosthesis which is adapted to cover said first through bore.

* * * * *

REEXAMINATION CERTIFICATE (2405th)
United States Patent [19]
Rangert et al.

[11] B1 5,069,622
[45] Certificate Issued  Sep. 27, 1994

[54] SPACER

[75] Inventors: Bo Rangert, Mölnlycke, Lars Jörnéus; Claes Holmberg, both of Gothenburg; Matts Andersson, Faker, all of Sweden

[73] Assignee: Nobelpharma AB, Gothenburg, Sweden

Reexamination Request:
No. 90/003,331, Feb. 9, 1994

Reexamination Certificate for:
Patent No.:   5,069,622
Issued:       Dec. 3, 1991
Appl. No.:    512,499
Filed:        Apr. 20, 1990

Related U.S. Application Data

[63] Continuation of Ser. No. 271,824, Nov. 16, 1988, abandoned.

[30] Foreign Application Priority Data

Nov. 18, 1987 [SE] Sweden .................. 8704514-2

[51] Int. Cl.$^5$ .................................................. A61C 8/00
[52] U.S. Cl. .................................................. 433/173
[58] Field of Search ................ 433/173, 174, 175, 176

[56]       References Cited
       U.S. PATENT DOCUMENTS 3,067,740  12/1962  Haboush .
3,732,621   5/1973  Bostrom .
3,987,499  10/1976  Scharbach et al. .
4,177,562  12/1979  Miller et al. ........................ 433/174
4,187,559   2/1980  Grell et al. .
4,416,629  11/1983  Mozsary et al. .................... 433/174
4,531,915   7/1985  Tatum, Jr. ........................... 433/173
4,547,157  10/1985  Driskell ............................... 433/173
4,693,724   9/1987  Rhenter et al. ...................... 623/23
4,713,003  12/1987  Symington et al. ................ 433/173
4,822,370   4/1989  Schelhas ............................. 623/23
5,015,186   5/1991  Detsch ................................ 433/173
5,080,685   1/1992  Bolesky et al. ..................... 623/23
5,181,928   1/1993  Bolesky et al. ..................... 623/23

FOREIGN PATENT DOCUMENTS

2413883  9/1975  Fed. Rep. of Germany .
2576793  8/1986  France .

*Primary Examiner*—Cary E. O'Connor

[57]       ABSTRACT

An angulated spacer element adapted is at its one end for attachment to a fixture having a threaded aperture and implanted in the jaw bone, and to support a dental prosthesis at the other end. The spacer element, which is a unitary member, has a first portion with an end surface thereof permitting abutting engagement with the protruding end of the implanted fixture. The first portion also has a through bore aligned with the threaded aperture in the fixture and defining an internal ledge to enable a screw to pass through the bore, abut the ledge and threadably engage the threaded aperture in the fixture. The first portion is adapted for locking the spacer element in a selectable one of a plurality of rotational, fixed positions in relation to the protruding portion of the fixture. The unitary spacer element also includes a second portion for supporting the dental prosthesis on the spacer element, the second portion forming an acute angle with respect to the through bore of the first portion.

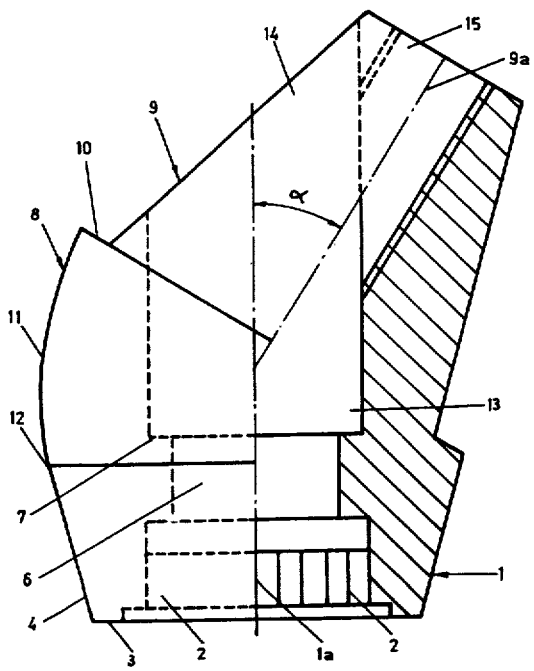

REEXAMINATION CERTIFICATE ISSUED UNDER 35 U.S.C. 307

NO AMENDMENTS HAVE BEEN MADE TO THE PATENT.

AS A RESULT OF REEXAMINATION, IT HAS BEEN DETERMINED THAT:

The patentability of claims 1-10 is confirmed.

* * * * *